US008023617B2

(12) United States Patent
Blendl et al.

(10) Patent No.: US 8,023,617 B2
(45) Date of Patent: Sep. 20, 2011

(54) METHOD AND DEVICE FOR QUALITY MANAGEMENT IN MAMMOGRAPHY APPARATUS

(75) Inventors: Christian Blendl, Bergheim (DE); Karl Lehi Schwartz, Pyrbaum (DE)

(73) Assignee: Ion Beam Applications S.A. (BE)

( * ) Notice: Subject to any disclaimer, the term of this patent is extended or adjusted under 35 U.S.C. 154(b) by 183 days.

(21) Appl. No.: 12/516,113

(22) PCT Filed: Nov. 26, 2007

(86) PCT No.: PCT/EP2007/062832
§ 371 (c)(1),
(2), (4) Date: May 22, 2009

(87) PCT Pub. No.: WO2008/062072
PCT Pub. Date: May 29, 2008

(65) Prior Publication Data
US 2010/0054401 A1 Mar. 4, 2010

(30) Foreign Application Priority Data
Nov. 24, 2006 (EP) .................................. 06124777

(51) Int. Cl.
*A61B 6/04* (2006.01)
(52) U.S. Cl. .......................................... 378/37; 378/165
(58) Field of Classification Search ............... 378/37, 378/62, 162, 165, 207
See application file for complete search history.

(56) References Cited

U.S. PATENT DOCUMENTS

| | | | |
|---|---|---|---|
| 4,764,948 A | 8/1988 | Hurwitz ............... | 378/165 |
| 5,506,884 A | 4/1996 | Goodenough et al. ..... | 378/207 |
| 5,994,900 A | 11/1999 | Gurvich ................ | 324/300 |
| 6,454,460 B1 | 9/2002 | Ramanathan et al. ..... | 378/207 |
| 6,556,698 B1 | 4/2003 | Diano et al. ............ | 382/132 |
| 2002/0181661 A1 | 12/2002 | Vafi et al. .............. | 378/207 |
| 2004/0081284 A1 | 4/2004 | Livingston ............. | 378/162 |
| 2004/0202359 A1 | 10/2004 | Muller et al. | |
| 2004/0245447 A1 | 12/2004 | Karasawa .............. | 250/252.1 |
| 2005/0173640 A1 | 8/2005 | Nascetti et al. ........ | 250/370.09 |

FOREIGN PATENT DOCUMENTS

| | | |
|---|---|---|
| DE | 8907423 U1 | 9/1989 |
| DE | 19520360 A1 | 12/1996 |
| WO | 2004/049949 A1 | 6/2004 |

OTHER PUBLICATIONS

M. Gambaccini et al., "A Performance Device For Quality Control In Mammography" Dosimetry in Diagnostic Radiology Seminar, Mar. 1991, vol. 43, No. 1-4, pp. 279-281.

*Primary Examiner* — Courtney Thomas
(74) *Attorney, Agent, or Firm* — Fitch, Even, Tabin & Flannery

(57) ABSTRACT

The present invention relates to a device and method for quality management (5) in a mammography apparatus (10), said apparatus comprising an X-ray source capable of directing a X-ray beam, a breast immobilization means (16, 18), and an X-ray image sensor system (20), said X-ray image sensor system (20) comprising a central area for sensing an image of said breast, and a peripheral area not used for imaging said immobilized breast. According to the invention, the device comprises a sensor for quality management (30), said sensor comprising a radiation dose detector in the path of said X-ray beam, for producing a dose measurement, and radiation absorbing elements (130, 350, 360, 380, 390, 400) for producing a detectable image of said X-ray beam on said X-ray image sensor system (20), acquisition means (20, 50, 60) for acquiring a digital image of said breast, and of said sensor for quality management (30), computing means (70) for computing quality management data (80) from said digital image of said sensor for quality management (30), and from said dose measurement.

20 Claims, 5 Drawing Sheets

\* = point
X = reference

METHOD AND DEVICE FOR QUALITY MANAGEMENT IN MAMMOGRAPHY APPARATUS

CROSS REFERENCE TO RELATED APPLICATIONS

This application is a national phase application of International Application No. PCT/EP2007/062832, filed Nov. 26, 2007, claiming priority to European Patent Application No. 06124777.1, filed Nov. 24, 2006, both of which are incorporated by reference herein in their entirety.

TECHNICAL FIELD

The invention relates to the field of mammography. More particularly, it relates to a device and method for quality control of the physical and technical aspects of mammography.

DESCRIPTION OF RELATED ART

Nowadays, mammography and other radiography examinations are performed on a regular basis for detecting tumors and other diseases. A mammography apparatus comprises an X-ray source, a breast immobilization device, a bucky table and an image sensor. Traditionally, film screen systems as sensors were used. These sensor types have the drawback that they need a processing phase (developing, fixing a.s.o.), and therefore the evaluation of the results of the examination, and of the quality of the image could not be performed in real-time. Nowadays, CR (Computed Radiography using luminescence sensors or storage phosphor plates) or DR (Digital Radiography, using semiconductor sensors) allow a real-time evaluation of the quality of the images. Both DR and CR sensors have a pixel structure, and are provide therefore images that are not translation- and rotation-invariant.

The use of mammography is being used for screening asymptomatic patients is considered justified. Mammography is also used as follow up during of after treatment (curative mammography). There is a need to high-quality images for improving the detection of cancers, and a contradicting need of minimizing the dose to the patient. Document "European Protocol for Dosimetry in Mammography", September 1998—EUR 16263—ISBN 92-827-7290.

For performing quality control of a mammography X-ray apparatus, it is known to perform daily, weekly, monthly or yearly quality control checks. These checks are usually performed by obtaining an image of a test object also known as a phantom, having different known radiation absorbing characteristics. Some phantoms have areas of different thicknesses, in a material simulating breast tissue. Some have elements simulating features to be detected such as microcalcifications, fibrous structures and tumours. The CDMAM phantom (Contrast Detail Phantom for Mammography) is an aluminium plate 0.5 mm thick, having thereon gold discs of different diameters and thicknesses, embedded in a 20 mm PMMA plate. The CIRS model 011A is an epoxy body, of a size simulating a compressed breast (length 12.5 cm, width 18.5 cm), and containing objects simulating defects to be detected.

DICOM (Digital Imaging and Communications in Medicine) is a comprehensive set of standards for handling, storing, printing and transmitting information in medical imaging. It includes a file format definition and a network communications protocol. DICOM files consist of a header with standardized as well as free-form fields and a body of image data. A single DICOM file can contain one or more images, allowing storage of volumes and/or animations. DICOM files group information together into a single data set. That is, a digital radiography image is in the same file as a patient ID, so that the image is never mistakenly separated from other information. Mammography apparatuses with DR X-ray image sensor are known which have an acquisition of the primary voltage in the transformer of the X-ray tube (kV), the charge through the tube during exposure (product of current and time, mAs) and entrance dose data. But the voltage at the secondary of the transformer is unknown or only estimated or calculated from the primary voltage and the settings for the transformation ratio. Mammography apparatuses with CR systems don't get any technical info from the apparatus into the Dicom header.

PRIOR ART DISCUSSION

The document US 2004/0202359 describes a method of evaluation of the quality of a radiographic image. This method uses a phantom such as the CDMAM phantom ordinarily used in mammography, comprising an aluminium plate 0.5 mm thick, on which gold chips of variable diameter and thickness are fastened. However, this method requires a large phantom for evaluating various statistical parameters, and therefore cannot be used for assessing the technical image quality for each breast image in real-time. These tests with CDMAM Phantom are performed with fixed settings of the exposure. Other exposures, used in exposing real mammaes can not be tested or analysed. A proven statistical analysis of all the different modes of the X-ray apparatuses is not available out of these tests with CDMAM phantoms or other test devices, such as the test device described in DIN PAS 1054. With these test devices, an analysis of the image of the mammae is not performed, neither in the Fourier space nor or in real space.

Document DE 19520360 discloses a method for checking stability of an X-ray generator for diagnostic applications. The method involves inserting a reference body into the beam path and switching off the test process when a defined switch-off dose is reached. The X-ray tube current is measured continuously and the charge input up to the point of switch-off is determined by integrating the current over the duration of the test procedure. The duration of the test procedure is independently measured and a computer compares these values with those of the initial conditions and forms differences which are output as a test report. Although this method allows determining the stability of an X-ray source, it does not allow performing quality management of other components and parameters of a radiography apparatus such as image quality, image contrast, sharpness, noise etc.

Document WO 2004/049949 discloses a mammography method and apparatus wherein information about breast immobilization paddles position, force, and duration are provided, together with other X-ray source pulse information, and manual input of data, to a tissue exposure control calculator that computes and displays technical factors for an X-ray exposure, such as X-ray tube voltage, X-ray tube current or exposure time. However, no means are provided for ascertaining the quality of the image, and for acquiring and storing the actual dose to the patient.

It is an object of the present invention to provide a device and method for quality management in a digital mammography apparatus which aims to overcome the above discussed disadvantages of the prior art. It is desired to improve the quality management of each exposure, for ensuring the quality of the patient clinical results, as well as minimizing the dose to the patient. It is also desired to improve the quality management of the apparatus used for performing these examinations, and to save time in the daily, weekly, monthly or yearly QA tests with test devices.

SUMMARY OF THE INVENTION

The present invention is related to a device and a method for quality management for a mammography apparatus, as well as a computer programme product as described in the claims.

DETAILED DESCRIPTION OF THE INVENTION

Figure 1:
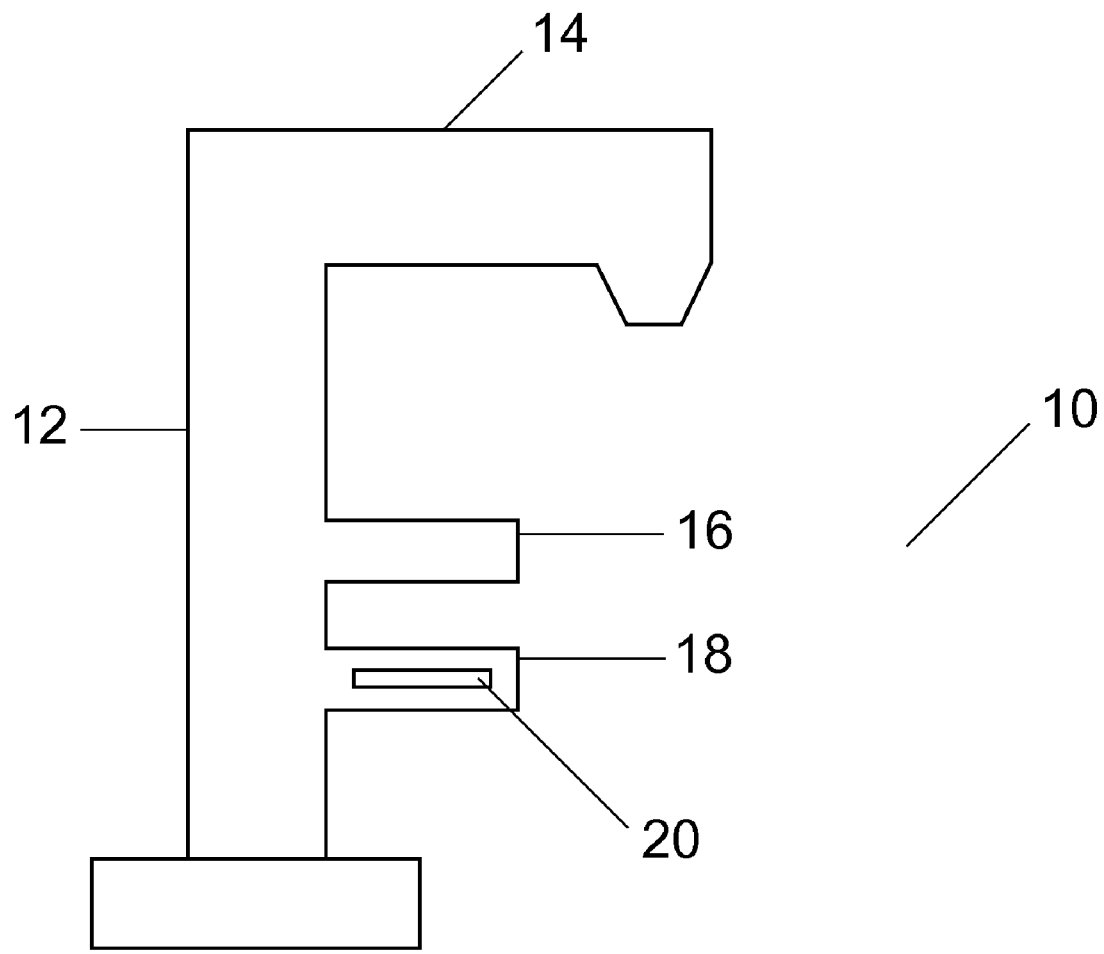
FIG. 1 is a schematic view of a mammography apparatus known in the art.

According to a preferred embodiment, the invention is directed to a device for quality management in a mammography apparatus. The mammography apparatus comprises an X-ray source capable of directing a X-ray beam, a breast immobilization means, i.e. a compression paddle and a bucky table, and an X-ray image sensor system. This X-ray image sensor system comprises a central area for sensing an image of said breast, and a peripheral area not used for imaging said immobilized breast. The device comprises:
  a sensor for quality management said sensor comprising a radiation dose detector in the path of said X-ray beam, for producing a dose measurement, and radiation absorbing elements for producing a detectable image of said X-ray beam on said X-ray image sensor system;
  acquisition means for acquiring a digital image of said breast, and of said sensor for quality management;
  computing means for computing quality management data from said digital image of said sensor for quality management, and from said dose measurement.

In a preferred embodiment, the device comprises a statistical analysis workstation for storing a plurality of quality management data for performing an optimization of the working mode of the mammography apparatus, and/or an optimization of the quality assurance of the mammography apparatus.

Preferably, the computing means comprise means for providing a formatted file comprising the digital image of said breast, associated with corresponding quality management data. The formatted file can be formatted according to the Dicom standard.

The quality management data may contain one or more of the following data:
  the dose measured by the sensor for quality management [Gy];
  the dose rate provided by same sensor [Gy/h];
  the exposure time;
  position number of angular position of coding disk;
  the thickness of the immobilized breast [mm];
  the actual energy [kV] of the X-ray beam;
  distance from the edge of the X-ray image sensor system to the side 'A' of the breast immobilization means;
  angular mismatch between an edge of the X-ray image sensor system, and the side 'A' of the breast immobilization means;
  the signal-to-noise ratio (SNR);
  contrast-to-noise ratio (CNR);
  modulation transfer function (MTF);
  the beam quality (HVL);
  the expected energy [kV] of the X-ray beam;
  the average glandular dose, calculated by the mammography apparatus, AGDma;
  the current in the X-ray tube;
  the compression distance between the compression paddle and the bucky table;
  the product of the X-ray tube current and the duration of the irradiation, i.e. the charge through the X-ray tube during the irradiation [mAs];
  the average glandular dose calculated by the quality management device, AGDqm;
  the patient identification data and age;
  the X-ray source voltage [kV];
  the spatial resolution;
  the threshold contrast visibility.

According to a preferred embodiment, the invention relates to a method for quality management in mammography comprising the steps of:
  providing a sensor for quality management in the path of an X-ray beam;
  acquiring a digital image of an exposure of a patient breast, and of said sensor for quality management;
  computing a second data set from said digital image of said sensor for quality management.

The method preferably further comprises the steps of:
  acquiring a first set of technical data from said sensor for quality management;
  acquiring said second set of technical data set;
  acquiring a third data set, characterizing the mammography process;
  grouping in a quality management data set, for each exposure, the data coming from each of the first, second and third data set.

The method, more preferably, comprising the steps of storing a plurality of quality management data for a plurality of image exposures with a mammography apparatus;
  performing an optimization of the working mode of said mammography apparatus, and/or an optimization of the quality assurance of said mammography apparatus, based on a statistical analysis of said plurality of quality management data.

According to a preferred embodiment, the invention provides a sensor for quality management in a mammography apparatus, comprising one or more of the following components;
  means for determining dose and dose rate of an X-ray beam;
  means for determining energy of an X-ray beam;
  means for determining the resolution of an X-ray image sensor system;
  means for identifying a specific image exposure in a sequence of successive image exposures taken with a mammography apparatus.
  means for defining the geometrical position of an X-ray image sensor system in respect to a bucky table;

Preferably, in the sensor, the means for determining the resolution of an X-ray image sensor system comprise a square plate and/or a rectangular plate, said plates being made of a radiation absorbing material, said plates having an angle with respect to a edge of said sensor.

In a preferred embodiment, the invention provides a computer program product comprising code for executing the methods and/or for cooperating with the devices and/or the sensors of the invention.

FIG. 1 is a general schematic view of a known mammography apparatus 10. A structure 12 carries a first arm 14 on which an X-ray source is installed. A second arm carries a breast compression paddle 16, and a third arm carries a bucky table 18, also known as a breast tray. An X-ray image sensor system 20 receives X-rays emitted from the X-ray source after passing through said compression paddle 16 and patient breast. All three arms are moveable along the structure 12, and this structure may in turn be moveable in translation and rotation movements. All these movements are controlled by an operator so as to give the optimal geometry, depending on patient size, etc. Means are provided for measuring and acquiring the distance between the compression paddle 16 and the bucky tray 18.

Figure 2:
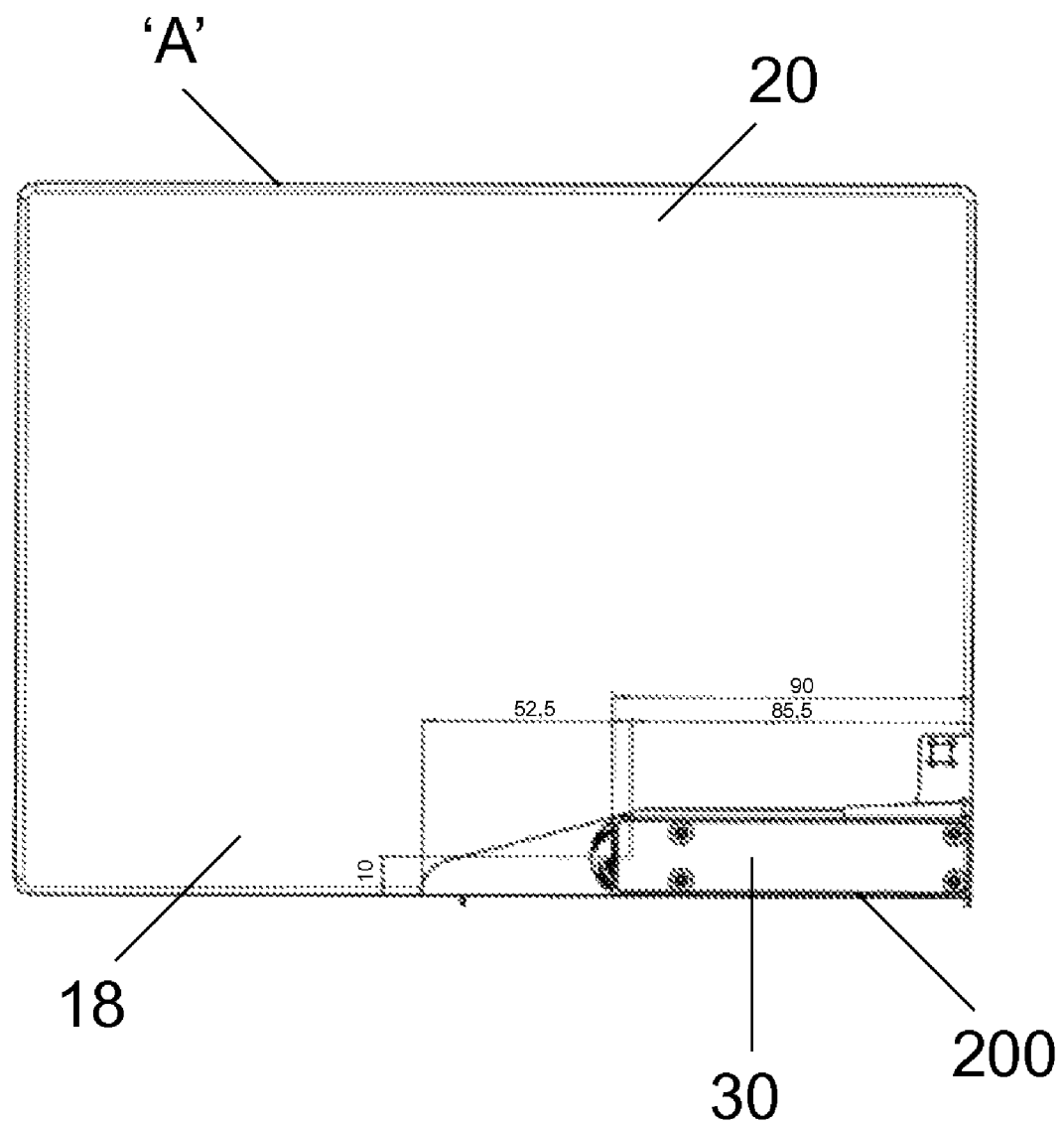
FIG. 2 is a top view of a bucky table for use in a mammography apparatus, wherein a sensor for quality management according to the invention is installed.

FIG. 2 is a top view of a bucky table 18 for use in a mammography apparatus. The patient thorax is applied along side 'A', with a breast above the table 18. Inside or below the tray 18, an X-ray image sensor system 20 is installed. This imaging device may be an electronic sensor, such as a flat panel, also called DR (Direct Radiography) or a luminescence foil, also called CR (Computer Radiography). According to the invention, a sensor for quality management 30 is installed in an angle of the breast tray 18 located near the supporting arm and structure 12, i.e. away from the side 'A' where a patient breast is introduced in the apparatus. By selecting this location, the sensor for quality management 30 is located in an area of the image sensor that is not used in a patient mammography. The sensor for image quality management of the invention 30 comprises at least one of the following elements:

means for determining dose, dose rate of the X-ray beam and/or exposure time;
means for determining energy of the X-ray beam;
means for determining the resolution of the X-ray image sensor system 20;
means for identifying a specific image exposure in a sequence of successive image exposures taken with a mammography apparatus;
means for determining the geometrical position of the X-ray image sensor system 20 relative to the bucky table 18;
means for determining the time of exposure (time stamp).

Each of these elements is discussed in more detail in the following paragraphs.

Referring to FIG. 2, the sensor for quality management 30 comprises a box 200. In this box 200, made of an X-ray transparent material, a set of three stacked diodes or other dose measurement device, such as ionization chamber, is installed. A set of radiation absorbing filters of different attenuating materials and thicknesses are installed above each of the detectors. These filter elements are chosen so that the filters exhibit different radiation absorption characteristics within the given voltage range. The diodes receive the attenuated radiation as it passes through the different filters and provide signals of different magnitudes. The ratio of the signals from the diodes at any instant in time is a function of the X-ray tube voltage (kVp) at that time, and thereby gives the energy of the X-ray beam. The signal from each detector can also be integrated over the exposure time and then the ratio of the integrated signals taken. This provides a different measure of tube potential, kV. This principle of kV detection of X-ray systems is well known in the art in a variety of stand alone meters. Also, the electronic components for transmitting the measured dose, as well as other acquired technical data, are installed in this box 200. The total dose of a single exposure can be recorded, as well as the dose rate (i.e. dose per unit time) and the exposure time.

Figure 3A:
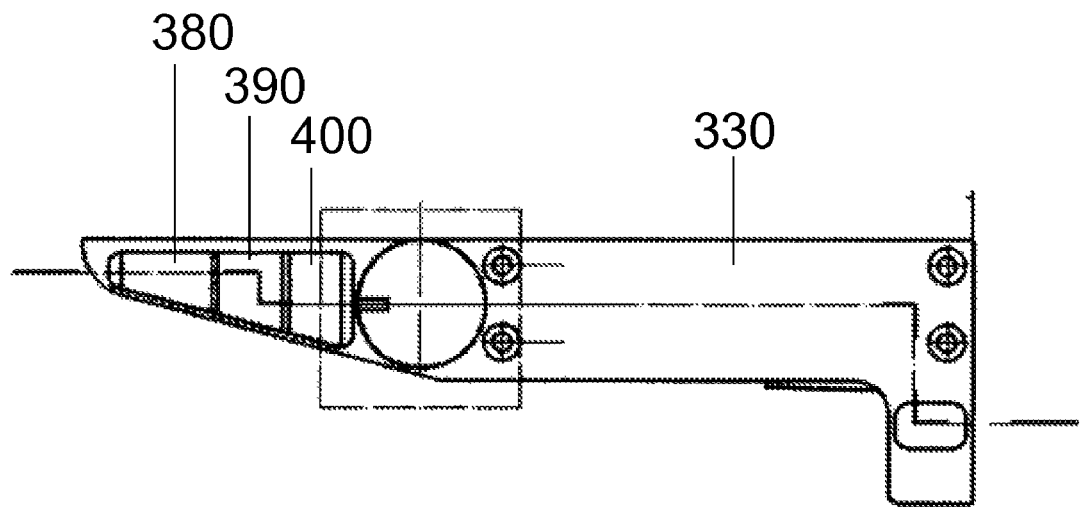
FIGS. 3a and 3b are bottom and top views of a sensor for quality management for use in the invention.

The FIG. 3a is a bottom view of the support plate 330 for a sensor 30 of the invention. The sensor for quality management 30 comprises the following components: a support plate 330 for supporting different test objects. This support plate 330 is a 2 mm tick plate made of an X-ray transparent material, such as carbon fibre reinforced plastic. In the bottom side of this plate, three hollows are provided for containing three aluminium plates 380, 390, 400, having a thickness of, respectively, 0.3, 0.5 and 0.7 mm. By measuring the X-ray absorption of these plates 380, 390, 400 on X-ray image sensor system 20, one can determine the Half Value Layer (HVL). The HVL is the thickness of aluminium-equivalent absorber which attenuates the air kerma of an X-ray beam by half. From the HVL, the energy of the X-ray beam can be determined by known techniques. This measurement of the energy can be compared with the energy value obtained from the stacked diodes in box 200. From the comparison of these two energy measurements, a quality assurance of the mammography apparatus and method is obtained.

Figure 3B:
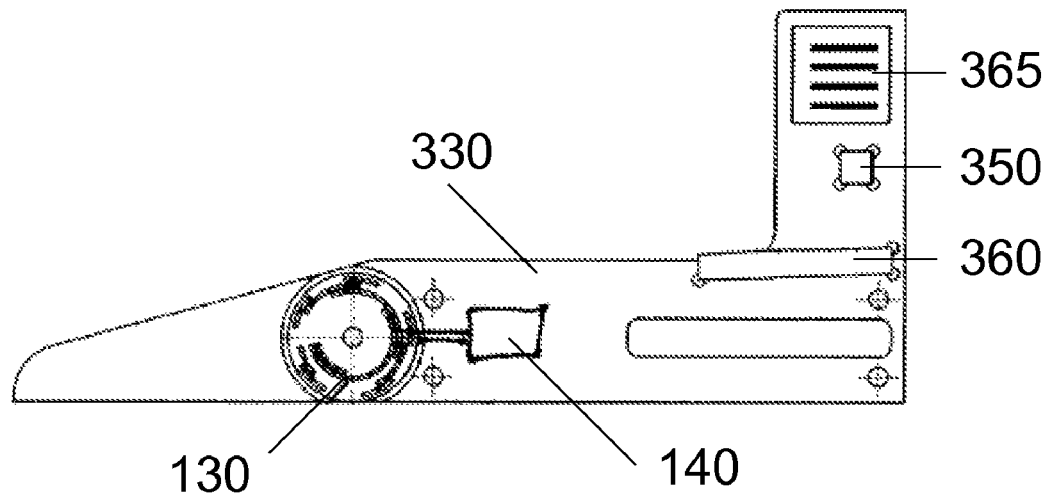

Referring to FIG. 3b, two hollows are provided on the top side of support plate 330. Thin rectangular plates 350, 360 of absorbing material are laid in these hollows. These hollows are slightly inclined with respect to the X-Y axis of the imaging device underneath. An angle of 2° is appropriate. By analyzing the image produced, one can determine the Modulation Transfer Function (MTF), and thereby, the resolution of the apparatus. A square 350 and an elongated rectangle 360 are used. Both are made of a strongly absorbing material such as iron (Fe) or tungsten (W) having a thickness of at least 1 mm. A pattern 365 of a material with a high atomic number, e.g. lead (Pb), molybdenum (Mo) or tungsten (W) is used to offer the possibility to check the visual resolution. One type of the available pattern which is used contains groups of lines pairs with 8, 10, 13 and 16 line pairs per mm (Lp/mm). The size of the pattern is about 15 by 15 mm. The other pattern which is available is made as a star pattern with an diameter of about 15 mm. By analysing the star pattern, an irregular pattern in the core of the pattern is achieved in which no resolution is detectable. An enlargement of this area of unsharpness indicates an enlargement of the size of the focus. This enlargement could be one or bidirectional.

Referring to FIG. 3b, one hollow is provided on the top side of support plate 330. A thin square plate 350 of absorbing material is laid in this hollow. This hollow is perpendicular with respect to the X-Y axis of the bucky table 18 underneath. By analyzing the image produced by this square plate 350, one can determine the geometrical position of the X-ray image sensor system 20 relative to the bucky table 18, and thereby, the non imaged breast area caused by the distance between the edge of bucky table 18 and the X-ray image sensor system 20. This square plate 350 is made of a strongly absorbing material such as iron (Fe) or tungsten (W) having a thickness of at least 1 mm.

Figure 4:
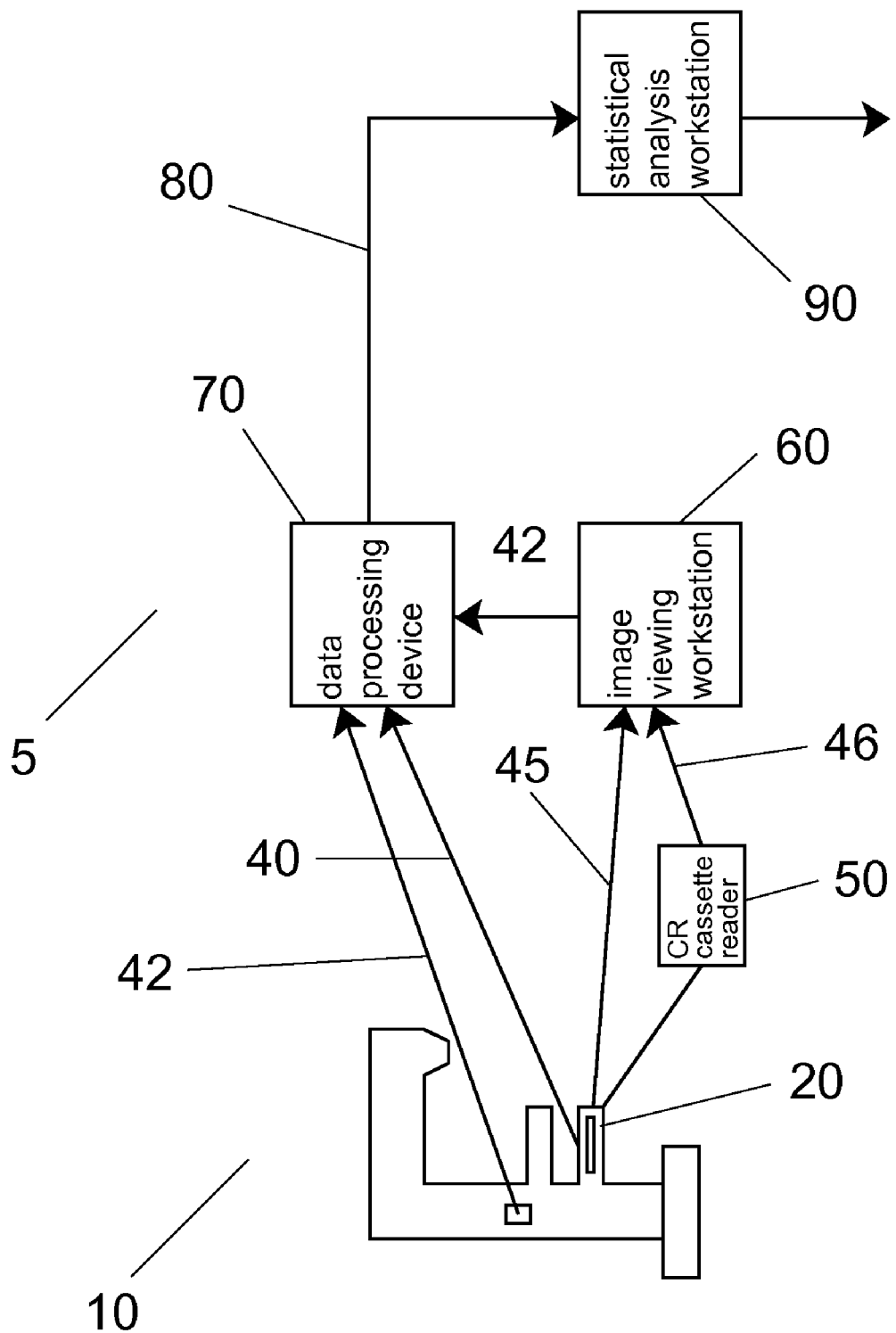
FIG. 4 is a schematic view of device for quality management for use in a mammography apparatus.

Referring to FIG. 4, the image data, acquired by X-ray image sensor system 20 are sent directly to a image viewing workstation 60 for direct observation. In the case of DR images, these data are sent directly. In this case, the link between the acquired technical data 40 and the acquired image data 45 is made simply by the fact that they are acquired simultaneously. When using a CR imaging system, a manual operation of reading the CR cassette is performed in a CR cassette reader 50. This manual operation breaks the simultaneity of acquisition of the acquired technical data 40 and the image data 45. Moreover, the operator could process successive CR cassettes in a order different from the order of exposure. Therefore, a means for identifying each successive CR image has been devised as follows: The sensor for quality management 30 is provided with an angular coding disk. Such angular coding disks are well known in other applications. They comprise, at different radiuses on the disk, sectors marked in a recognizable way. The radiuses and sectors are selected such that, by examining the image on a radius of the disk, the angular position of the disk can be determined. In the present application, the sector are marked with a radiation opaque material, and a radiation transparent gap is provided so that a coding of the angular position, among twenty distinct angles, can be detected on an image acquired through the X-ray image sensor system 20. A motor 140 is provided in the box 200. This motor rotates disk 130 from a determined angle (i.e. 18', for a 20 position disk) for each successive exposure.

The device for quality management of the invention is represented in FIG. 4 as a block diagram. A first set of acquired technical data 40 is sent directly from the sensor for quality management 30 to a data processing device 70:
- the dose measured by the sensor for quality management 30 [Gy];
- the dose rate and/or exposure time provided by same [Gy/s]; by plotting successive values of the dose rate during an exposure, a waveform of the X-ray intensity is obtained.
- the exposure time;
- position number of angular position of coding disk.

A second set of data 41 is determined from an analysis of the image data, being either the acquired DR image 45, when using a DR-sensor, or the acquired CR image 46 when using a CR-sensor and a CR cassette reader 50. In both cases, an analysis is performed in an image viewing workstation 60, and provides the following second set of data:
- the actual energy [kV] of the X-ray beam is determined from the image area showing the three aluminium plates 380, 390, 400;
- position number of image of coding disk;
- The distance from the edge of the X-ray image sensor 30 to the side 'A' of the bucky table 18 where a patient breast is introduced;
- Any angular mismatch between an edge of the X-ray image sensor system 20, and the bucky table 18;
- Different Signal-to-noise ratios (SNR) (behind each Al filter the SNR can be calculated);
- Different Contrast-to-noise ratio (CNR) (between two Al filters the CNR can be calculated);
- Modulation transfer function (MTF) as a scientific value of the Spatial Resolution the used material of the anode and the additional filter calculated with the Al-HVL (Aluminium Half Value Layer) and the dose rate to calculate the Mean Glandular Dose (MGD).
- Beam quality (Al-HVL);

The last parameters are determined from the image area showing the square 350 and an elongated rectangle 360 using methods known in the art, as stated e.g. in PAS 1054 or to IEC 61223-3. This second set of data is then sent from image viewing workstation 60 to data processing device 70.

A third set of data 42 is provided by the mammography apparatus 10 itself to the data processing device 70:
- the expected energy [kV] of the X-ray beam, as determined by the primary voltage of the X-ray tube power supply and the setting of the ratio of the transformer used;
- the average glandular dose, calculated by the mammography apparatus, $AGD_{ma}$ in a way well known in the art, based on patient age, machine settings for kV and mAs, thickness of the compressed breast, and anode-filter combination;
- the current in the RX-tube [mA];
- the compression distance between compression paddle 16 and the bucky table 18.

This last data may be provided by a special sensor added to the mammography apparatus. The measurement device for the compression distance may comprise a magnetic incremental lift encoder and a scanning sensor. The scanning sensor is mounted on the compression paddle support (16) and a magnetic tap is installed on the guide rail of the mammography apparatus. Depending on the compression distance, the scanning sensor generates counter pulses (TTL Signals) and the conversion of pulses is representative for the compression distance.

The device for quality management of the invention comprises a data processing device 70 performing the following functions:
- grouping in a single record, the quality management data set 80, for each exposure, the data coming from each of the first 40, second 41 and third 42 data set;
- determining and adding to the record the following data:
  - the product of the tube current and the duration of the irradiation, i.e. the charge through the tube during the irradiation [mAs];
  - the average glandular dose calculated by the quality management device, $AGD_{qm}$, based on the same parameters as above, but taking the acquired values of these parameters;
  - patient identification data and age;
  - the irradiation duration [ms];

This record is preferably organized as a DICOM-compliant record, and contains all above cited-data, as well as the image of the exposure. This record is sent by the data processing device 70 to the statistical analysis workstation 90.

The device for quality management of the invention also comprises a statistical analysis workstation 90 This workstation stores all successive quality management data sets 80. Acquiring and storing the quality management data 80 together with the image data for each exposure allows the statistical analysis of this set of data for attaining the following purposes:
- optimize the working mode(s) of the mammography apparatus;
- optimize the quality assurance of the mammography apparatus.

Figure 5:
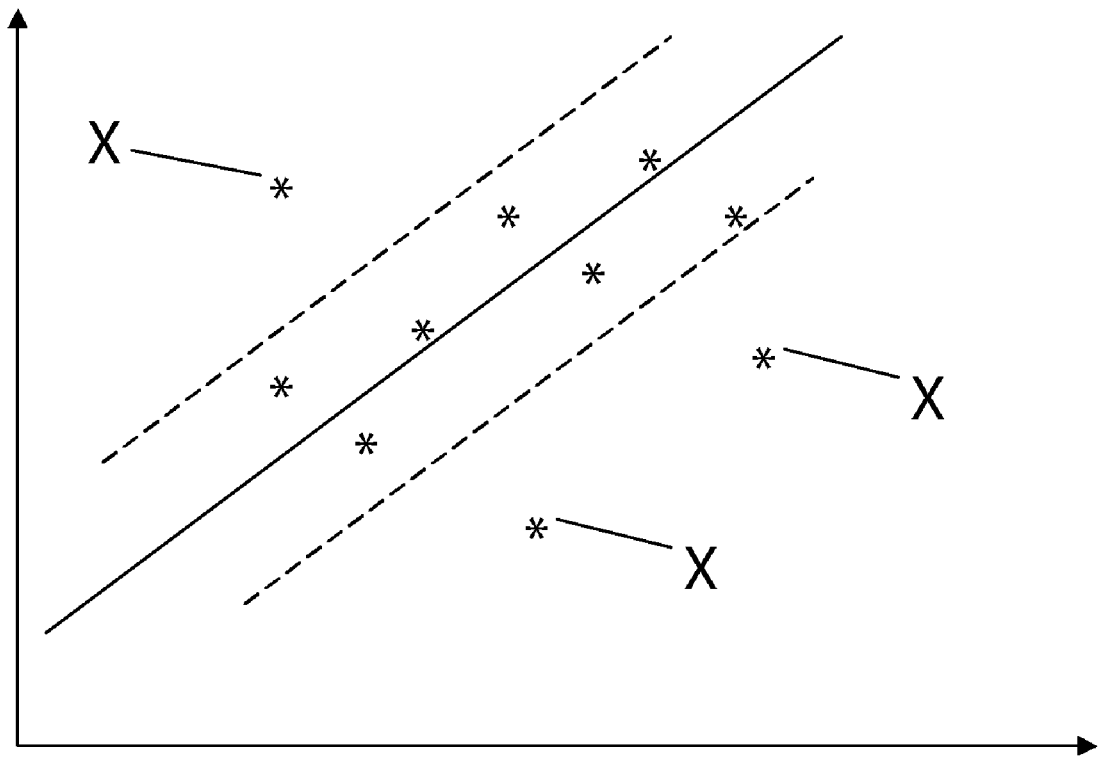
FIG. 5 is an example of a plot used for statistical analysis of the quality management data.

The optimization of the working mode of the mammography apparatus is performed as follows: a data A, related to a data B are plotted in a linear regression plot exemplified on FIG. 5, where values A, B of an exposure are represented by a point. Points are scattered around a regression line. The statistical analysis entails the observation of points X that are beyond the 2 σ line around regression line. The occurrence of such points is an indication of some malfunction of the mammography apparatus. If a representative point of the exposure of the patient currently being examined lies beyond the 2 σ line, a conclusion may be drawn that something went wrong in this exposure. The working parameters of the mammography apparatus may then be adapted for correcting the default. On the other hand, by analyzing the statistical results of a large number of exposures, on may observe that the 2 σ line lies two far away from the expected values. In this case, a malfunction of the apparatus may be inferred. Among the couples of data A, B that may be used for such statistical analysis are the following couples, listed as examples:

1) Couples, which are used to control values given by the apparatus:

exposure time: to control changes in triggering the signals;

dose rate: to detect changes in the surface of the anode, which lowers the dose rate and/or the dose yield (Dose per mAs). These changes can not be detected by calculated values.

Tube Voltage [kV]: to detect changes in the surface of the anode, which change the beam quality (beam hardening) and which can not detected by calculated values. The expected tube voltage (kV of the X-ray beam, as determined by the primary voltage of the X-ray tube power supply and the known ratio of the transformer, and the actual voltage [kV] of the X-ray beam as determined from the image of the three aluminum plates 380, 390, 400 and/or measured by the (Wellhöfer device);

Thickness of compression of the breast: both measurements influence the calculation of the Average Glandular Dose 2) Couples or values, which are used to analyse the exposure technique or to analyse technical values of each exposure in respect to others.

age: to control the age restrictions, which are made in screening programs;

Paraphe of the technician: to control the used and statistically analysed compression force of each technician and to harmonise the compression force to best practice between all technicians.

The Average Glandular Dose, as calculated by the mammography apparatus, $AGD_{ma}$, and the average glandular dose as calculated by the quality management device with measured datas: to control the $AGD_{qa}$ in respect to legal restriction and to correlate the $AGD_{qa}$ with the exposing values for each individual breast to analyse and optimize the used exposure technique (ALARA-Principle)

The Exposure Index, as calculated by the quality management device or by the mammography apparatus is based on the histogram of the image and can be used to control the dose at detector plane.

Signal to Noise Ration (SNR) or/and Contrast to Noise Ratio (CNR)), calculated in the image in correlation to other values, which describe the measured beam quality: these correlation can be used to differentiate between noise sources: beam quality or detector.

3) Values, which are produced by an analysis of the image of the mammae itself and which can correlate with the morphological composition (fat versus glandular tissue), the absorbing characteristics of different tissues, the used exposure technique and/or clinical diseases. These analyses with resulting values are a part of the quality management system. Some examples of applicable image processing methods are listed below:

histograms: deviations from an averaged histogram is useful;

frequency pattern: A Fourier analysis from each image shows the frequency content of a mammogram. Significant deviations from an averaged frequency spectra is useful.

noise power spectra: significant deviations from an averaged spectra is useful.

The statistical analysis performed on the data is similar to the statistical process control (SPC) method used in manufacturing industries for achieving quality control.

Although FIG. 4 represents image viewing workstation 60, data processing device 70, and statistical analysis workstation as separate computers, this is not required by the invention. Two of these computers, or all three may be grouped in a single one performing all the functions discussed. An integrated, single workstation may be preferred for a new mammography apparatus, while the separate design shown in FIG. 4 may be preferred for retrofitting the device for quality management of the invention to an existing mammography apparatus.

By using the device and method of the invention, the actual diagnostic image and the quality assurance data are collected in a single exposure. Thereby, no weekly or daily QA tests are needed any more. The monthly and yearly QA test are shortened to tests which can be performed in a few minutes or a few hours respectively, and quality assurance data are obtained in real time. In addition, these meta-data are stored, together with the image data, in a Dicom data file, thereby ensuring that all the relevant data are available for evaluation by a medical physicist or expert at a later time.

The invention claimed is:

1. A device for quality management for a mammography apparatus, the device including a sensor for quality management, the sensor comprising:

means for determining dose and/or dose rate of an exposure to an X-ray beam, the means configured for producing a first data set readable by a computing means;

a plurality of radiation absorbing elements configured for producing a detectable image of the exposure to the X-ray beam on an X-ray image sensor system, a second data set being derivable from an analysis of the detectable image; and image coding means for producing an identification code of the exposure on the X-ray image sensor system, an exposure identification code being derivable from an analysis of the detectable image.

2. The device according to claim 1, wherein the plurality of radiation absorbing elements comprises a plurality of absorbing plates, each plate having a different thickness, whereby energy of the X-ray beam is derivable from an analysis of the image.

3. The device according to claim 1, wherein the plurality of radiation absorbing elements comprises one or more absorbing rectangular plates of absorbing material, the rectangular plates having an angle with respect to an edge of the image sensor system, whereby resolution of the image sensor system is derivable from an analysis of the image.

4. The device according to claim 1, wherein the image coding means comprises an image coding wheel and a motor.

5. The device according to claim 1 wherein the computer means comprises:

means for acquiring and storing the first data set;

means for acquiring and storing the detectable image of the X-ray beam on the X-ray image sensor system;

means for analysing the detectable image for deriving the second data set;

means for analysing the detectable image for deriving the exposure identification code; and means using the exposure identification code for grouping in a quality management data set data of the first data set and data of the second data set corresponding to same exposure.

6. The device according to claim 1, wherein the device further comprises a statistical analysis workstation configured for:

receiving and storing a plurality of quality management data for a plurality of exposures with the mammography apparatus; and performing an optimization of working mode of the mammography apparatus, and/or an optimization of quality assurance of the mammography apparatus, based on a statistical analysis of the plurality of quality management data.

7. A method for quality management in mammography, the method comprising:

reading the value of dose and/or dose rate of an exposure to an X-ray beam, the dose and/or dose rate forming a first data set;

providing a plurality of radiation absorbing elements producing a detectable image of the exposure to the X-ray beam on an X-ray image sensor system;

providing image coding means for producing an identification code of the exposure on the X-ray image sensor system;

acquiring a digital image of the exposure of the X-ray beam;

analysing the digital image for deriving a second data set;

analysing the digital image for deriving an exposure identification code;

using the exposure identification code for grouping in a quality management data set the data of said the first data set and the data of the second data set corresponding to same exposure.

8. The method according to claim 7, the method further comprising:

acquiring a third data set, characterizing the mammography process;

grouping in the quality management data set, for each exposure, data coming from each of the first, second and third data set.

9. The method according to claim 7, wherein the method further the steps of:

storing a plurality of quality management data for a plurality of exposures with a mammography apparatus; and performing an optimization of the working mode of the mammography apparatus, and/or an optimization of quality assurance of the mammography apparatus, based on a statistical analysis of the plurality of quality management data.

10. A computer program product comprising code for executing the method of claim 7.

11. A system for quality management for a mammography apparatus, the system including a sensor for quality management, the sensor comprising:

a device configured to determine dose and/or dose rate of an exposure to an X-ray beam and configured to produce a first data set readable by a computer;

a plurality of radiation absorbing elements configured to produce a detectable image of the exposure to the X-ray beam on an X-ray image sensor system, a second data set being derivable from an analysis of the detectable image;

an image coding device configured to produce an identification code of the exposure on the X-ray image sensor system, an exposure identification code being derivable from an analysis of the detectable image.

12. The system according to claim 11, wherein the plurality of radiation absorbing elements comprises a plurality of absorbing plates, each plate having a different thickness, whereby energy of the X-ray beam is derivable from an analysis of the image.

13. The system according to claim 11, wherein the plurality of radiation absorbing elements comprises one or more absorbing rectangular plates of absorbing material, the rectangular plates having an angle with respect to an edge of the image sensor system, whereby resolution of the image sensor system is derivable from an analysis of the image.

14. The system according to claim 11, wherein the image coding device comprises an image coding wheel and a motor.

15. The system according to claim 11, wherein the computer comprises:

a device configured to acquire and store the first data set;

a device configured to acquire and store the detectable image of the X-ray beam on the X-ray image sensor system;

a device configured to analyze the detectable image for deriving the second data set;

a device configured to analyze the detectable image for deriving the exposure identification code; and a device configured to use the exposure identification code for grouping in a quality management data set data of the first data set and data of the second data set corresponding to same exposure.

16. The system according to claim 11, comprising a statistical analysis workstation adapted for:

receiving and storing a plurality of quality management data for a plurality of exposures with the mammography apparatus;

performing an optimization of working mode of the mammography apparatus, and/or an optimization of quality assurance of the mammography apparatus, based on a statistical analysis of the plurality of quality management data.

17. A method for quality management in mammography, the method comprising:

reading the value of dose and/or dose rate of an exposure to an X-ray beam, the dose and/or dose rate forming a first data set;

providing a plurality of radiation absorbing elements producing a detectable image of the exposure to the X-ray beam on an X-ray image sensor system;

producing an identification code of the exposure on the X-ray image sensor system;

acquiring a digital image of the exposure of the X-ray beam;

analyzing the digital image for deriving a second data set;

analyzing the digital image for deriving an exposure identification code;

using the exposure identification code for grouping in a quality management data set the data of the first data set and the data of the second data set corresponding to same exposure.

18. The method according to claim 17, the method further comprising:

acquiring a third data set, characterizing the mammography process;

grouping in the quality management data set, for each exposure, data coming from each of the first, second and third data set.

19. The method according to claim 17, comprising the steps of:

storing a plurality of quality management data for a plurality of exposures with a mammography apparatus;

performing an optimization of the working mode of the mammography apparatus, and/or an optimization of quality assurance of the mammography apparatus, based on statistical analysis of the plurality of quality management data.

20. A computer program product comprising code for executing the method claim 17.

* * * * *